United States Patent
Lin

(10) Patent No.: US 10,457,989 B2
(45) Date of Patent: Oct. 29, 2019

(54) METHOD OF DOUBLE ALLELE SPECIFIC PCR FOR SNP MICROARRAY

(71) Applicant: Phalanx Biotech Group, Inc., Hsinchu (TW)

(72) Inventor: Shang-Chi Lin, Hsinchu (TW)

(73) Assignee: Phalanx Biotech Group, Inc., Hsinchu (TW)

( * ) Notice: Subject to any disclaimer, the term of this patent is extended or adjusted under 35 U.S.C. 154(b) by 424 days.

(21) Appl. No.: 15/162,907

(22) Filed: May 24, 2016

(65) Prior Publication Data

US 2017/0183729 A1    Jun. 29, 2017

(30) Foreign Application Priority Data

Dec. 28, 2015    (TW) .............................. 104144049 A

(51) Int. Cl.
| | | |
|---|---|---|
| *C12P 19/34* | (2006.01) | |
| *C12Q 1/6883* | (2018.01) | |
| *C12Q 1/6827* | (2018.01) | |
| *C12Q 1/6858* | (2018.01) | |

(52) U.S. Cl.
CPC ......... *C12Q 1/6883* (2013.01); *C12Q 1/6827* (2013.01); *C12Q 1/6858* (2013.01); *C12Q 2600/156* (2013.01); *C12Q 2600/16* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 2003/0104372 A1* | 6/2003 | Ahmadian | C12Q 1/6858 435/6.11 |
| 2005/0214825 A1* | 9/2005 | Stuelpnagel | C12Q 1/6837 435/6.11 |
| 2014/0274786 A1* | 9/2014 | McCoy | C12Q 1/6844 506/9 |
| 2016/0258010 A1* | 9/2016 | Panousis | C12Q 1/6851 |

\* cited by examiner

*Primary Examiner* — Kenneth R Horlick
(74) *Attorney, Agent, or Firm* — Muncy, Geissler, Olds & Lowe, P.C.

(57) ABSTRACT

The present invention provides a method of double allele specific polymerase chain reaction (PCR) for single nucleotide polymorphism (SNP) microarray, the method provides the allele specific site as the 3' terminal nucleotide of forward and reverse primers, it does not require a primer having specific nucleotides. The method of the present invention is easily to design the primer based on flanking region of the allele specific site, and to perform multiplex SNP PCR applying with an interchelating agent, then to detect by a SNP microarray.

10 Claims, 1 Drawing Sheet
Specification includes a Sequence Listing.

rs29232

Tm : 62.5±1.4°C

AGAGATTATACTTGCAATGCTATCAAAATG        Tm=63.2
        AGAGATTATACTTGCAATGCTATCAAAATA        Tm=62.6

5'
GTGCATGCACCAGAGATTATACTTGCAATGCTATCAAAATRCTCATGGGTGGTGGGGATGCACAGAGGTC

CACGTACGTGGT CTCTAATAT GAACGTTACGATAGTTTTAYGAGTACCCACCACC C CCTACGTGT CTCCAG

Tm = 61.7  CGAGTACCCACCACC C        5'
        Tm = 63.2  TGAGTACCCACCACC C

METHOD OF DOUBLE ALLELE SPECIFIC PCR FOR SNP MICROARRAY

CROSS-REFERENCE TO RELATED APPLICATION

This application claims the priority of Taiwanese patent application No. 104144049, filed on Dec. 28, 2015, which is incorporated herewith by reference.

BACKGROUND OF THE INVENTION

1. Field of the Invention

The present invention is to provide a method of double allele specific PCR, and more particularly, to provide a method of double allele specific PCR for SNP microarray.

2. The Prior Arts

There are many different types of genetic variation in the human genome; the most studied class of variant is the single nucleotide polymorphism (SNP). SNPs lying in protein-coding regions of the gene can alter the code for an amino acid sequence and may affect the function of a protein and the regulation of a gene expression so as to cause disease.

Recently, high-throughput microarray chip technology has been wildly used to detect individual differences, to perform genetic correlation analysis, to analyze linkage disequilibrium or to screen drug metabolism genes, etc. However, the high-throughput microarray chip technology contains some defects: for example, the pre-treatment step prior to array hybridization is quite time-consuming, tens of thousands of SNPs data obtained after array screening are difficult to statistically analyze, and the instruments and suppliers are very expensive. Another technology, real-time polymerase chain reaction, is also wildly used due to its high specificity, sensitivity and accuracy, but it requires high cost to design a probe containing specific modification for each SNP, which results in higher overall costs for detection, and this technology is not suitable for large-scale SNP genotyping detection. Therefore, an effective, rapid, large-scale detection technology for singe nucleotide variation is needed.

SUMMARY OF THE INVENTION

As such, a primary objective of the present invention is to provide a method of double allele specific polymerase chain reaction (PCR) for single nucleotide polymorphism (SNP) microarray, comprising: (a) amplifying a nucleic acid sample by multiplex SNP PCR using at least a primer set which recognizes a single nucleotide polymorphism (SNP) to obtain an amplified product; wherein an interchelating agent is added into PCR, and the interchelating agent is SYBR® green dye; and (b) contacting the amplified product with a SNP microarray fixed a probe suitable for deteiinine the identity of SNP to genotype SNP, wherein the primer set contains at least four allele specific primers, which at least two allele specific primers bound with a sense strand of the nucleic acid sample, and 3' terminal nucleotides of the two allele specific primers are complementary to an allele specific site; and at least two allele specific primers bound with an antisense strand of the nucleic acid sample, and 3' terminal nucleotides of the two allele specific primers are complementary to the allele specific site.

Another objective of the present invention is to provide a method of double allele specific polymerase chain reaction (PCR) for single nucleotide polymorphism (SNP) microarray by identifying a modified label, comprising: (a) amplifying a nucleic acid sample by multiplex SNP PCR using at least a primer set which recognizes a single nucleotide polymorphism (SNP) to obtain a first amplified product; wherein an interchelating agent is added into PCR, and the interchelating agent is SYBR® green dye; (b) amplifying the first amplified product using a universal PCR primer having a modified label at 5' terminal end to obtain a second amplified product; and (c) contacting the second amplified product with a SNP microarray fixed a probe suitable for determine the identity of SNP to genotype SNP, wherein the sequence of the primer set contains two regions, which 5' terminal region of the allele specific primer is a universal PCR primer sequence, and 3' terminal region of the allele specific primer is an allele specific primer region; and wherein the primer set contains at least four allele specific primers, which at least two allele specific primers bound with a sense strand of the nucleic acid sample, and the 3' terminal region of the two allele specific primers are complementary to an allele specific site; and at least two allele specific primers bound with an antisense strand of the nucleic acid sample, and the 3' terminal region of the two allele specific primers are complementary to the allele specific site.

A further objective of the present invention is to provide a primer set for double allele specific polymerase chain reaction (PCR) applying with an interchelating agent, comprising: the primers contain four allele specific primers, wherein at least two allele specific primers bound with a sense strand of a nucleic acid sample, and 3' terminal region of the two allele specific primers are complementary to an allele specific site; and at least two allele specific primers bound with an antisense strand of the nucleic acid sample, and 3' terminal region of the two allele specific primers are complementary to the allele specific site.

A further objective of the present invention is to provide a primer set for double allele specific polymerase chain reaction (PCR) applying with an interchelating agent, comprising: the primer set contains four allele specific primers, wherein at least two allele specific primers bound with a sense strand of a nucleic acid sample, and 3' terminal region of the two allele specific primers are complementary to an allele specific site; and at least two allele specific primers bound with an antisense strand of the nucleic acid sample, and 3' terminal region of the two allele specific primers are complementary to the allele specific site; 5' terminal region of the four allele specific primers are universal PCR primer sequences.

According to an embodiment of the present invention, the interchelating agent is SYBR® green dye.

According to an embodiment of the present invention, the allele specific primers have similar melting temperature (Tm) values.

According to an embodiment of the present invention, the modified label is fluorescence, biotin, digoxigenin (DIG) or oligonucleotide sequence.

According to an embodiment of the present invention, the SNP microarray is detected by a fluorescent array imaging reader.

According to an embodiment of the present invention, the nucleic acid sample is obtained from blood, serum, plasma, body fluids or tissues.

According to an embodiment of the present invention, the allele specific primers further comprise a barcode sequence between the universal PCR primer sequence and the allele specific primer region; and the probe comprises a sequence complementary to the barcode sequence.

Accordingly, the present invention is to provide a method of double allele specific polymerase chain reaction (PCR) for single nucleotide polymorphism (SNP) microarray, a multiplex SNP PCR that can be used in accordance with the present method which may include using a SYBR® green dye and the amplified product can be detected by a SNP microarray. The method is to use the allele specific site as the 3' terminal nucleotide of forward and reverse primers; it does not require a primer having specific nucleotides such as LNA(locked nucleic acid) or PNA (peptide nucleic acid). Therefore, the method of the present invention is easily to design the primer for SNP array detection, and it does not require a primer having specific nucleotides and has an advantage of detecting a plurality of SNPs at the same time.

The accompanying drawings are included to provide a further understanding of the invention, and are incorporated in and constitute a part of this specification. The drawings illustrate embodiments of the invention and, together with the description, serve to explain the principles of the invention.

BRIEF DESCRIPTION OF THE DRAWINGS

The present invention will be apparent to those skilled in the art by reading the following detailed description of a preferred embodiment thereof, with reference to the attached drawings, in which:

Figure is a schematic diagram illustrating a primer design of the method of double allele specific polymerase chain reaction (PCR) for single nucleotide polymorphism (SNP) microarray.

DETAILED DESCRIPTION OF THE PREFERRED EMBODIMENT

The present invention provides a method of double allele specific polymerase chain reaction (PCR) for single nucleotide polymorphism (SNP) microarray, the method into use the allele specific site as the 3' terminal nucleotide of forward and reverse primers, it does not require a primer having specific nucleotides. The method of the present invention is easily to design the primer based on flanking region of the allele specific site, and to perform multiplex SNP PCR using with an interchelating agent, then to detect by a SNP microarray.

Definition

As used herein, a nucleic acid is deoxyribonucleic acid (DNA) or ribonucleic acid (RNA).

As used herein, a nucleotide is the basic unit of the nucleic acid.

As used herein, SYBR® green dye is a nucleic acid stain that binds double-stranded DNA molecules, emitting a fluorescent signal on binding. SYBR® green dye is a fluorescent dye that exhibits little fluorescence when in solution, but emits a strong fluorescent signal upon binding to double-stranded DNA. In particular, SYBR® green dye binds double-stranded DNA, and upon excitation emits light. SYBR® green dye includes but not limited to SYBR green I (cat #1988131, ROCHE).

EXAMPLE 1

Primer Design

The present invention provides a method of double allele specific polymerase chain reaction (PCR) for single nucleotide polymorphism (SNP) microarray, which includes a first amplifying section for amplifying an allele specific site, a second amplifying section for amplifying the product of the first amplifying section by using an universal primer; and detecting the allele specific site by a SNP microarray fixing a probe.

The technical feature of the present invention is the allele specific primers design, the method is to use a forward primer complementary to the allele specific site in one strand of DNA template and a reverse primer complementary to the allele specific site in the other strand of DNA template, which is significant different from the design of the traditional PCR primer. The method is to use the allele specific site as the 3' terminal nucleotide of forward and reverse primers; it does not require a primer having specific nucleotides and directly design the primer based on flanking region of the allele specific site. In the present embodiment, the present invention provides 5 SNPs, for example but not limited to, rs29232, rs401681, rs667282, rs2072590 and rs2131877. Note that, the primers in multiplex SNP PCR have similar melting temperature (Tm) values, Tm=4(G+C)+2(A+T).

For rs29232, as shown in Figure and Table 1, re29232 is a A/G genetic variation, the primer is designed from flanking region of the genetic variation site, the forward primers (SEQ ID NO:1 and SEQ ID NO:2) are respectively to using the genetic variation site A or G as the 3' terminal nucleotide of the forward primers, the reverse primers (SEQ ID NO:3 and SEQ ID NO:4) are respectively to using the genetic variation site C or T as the 3' terminal nucleotide of reverse primers, and amplifying gDNA using two sets of primers (AT primer set and GC set of primers), it does not require a primer having specific nucleotides. The primers of other SNPs: the primers of rs401681 are SEQ ID NO: 5 to SEQ ID NO: 8, the primers of rs667282 are SEQ ID NO: 9 to SEQ ID NO: 12, the primers of rs2072590 are SEQ ID NO: 13 to SEQ ID NO: 16 and the primers of rs2131877 are SEQ ID NO: 17 to SEQ ID NO: 20.

Regarding the primers of second amplifying section, as shown in Table 1, AT universal primer is modified with Cy3 at 5' terminus (SEQ ID NO:21), and GC universal primer is modified with Cy5 at 5' terminus (SEQ ID NO:22).

The present invention provides the probe fixed on SNP microarray for determining SNP variation site, including but not limited to rs29232 probe (SEQ ID NO: 23), rs401681 probe (SEQ ID NO:24), rs667282 probe (SEQ ID NO:25), rs2072590 probe (SEQ ID NO:26) and rs2131877 probe (SEQ ID NO:27) modified with ammine at 5' terminus fixed on a SNP microarray for hybridization reaction.

TABLE 1

| SEQ ID NO | oligo ID | oligo sequence |
|---|---|---|
| SEQ ID NO: 1 | AS-rs29232-fwdA | GATCAGGCGTCTGTCGTGCTCTGGAGAGATTATACTTGCAATGCTATCAAAAT<u>A</u> |
| SEQ ID NO: 2 | AS-rs29232-fwdG | CCTTCCTTCCTTCCTTCCTTCCTTTGGAGAGATTATACTTGCAATGCTATCAAAT<u>G</u> |
| SEQ ID NO: 3 | AS-rs29232-revC | CCTTCCTTCCTTCCTTCCTTCCTTAGGCCCACCACCCATGAG<u>C</u> |

Primer sequence

TABLE 1-continued

| SEQ ID NO | oligo ID | oligo sequence |
|---|---|---|
| SEQ ID NO: 4 | AS-rs29232-revT | GATCAGGCGTCTGTCGTG CTCTAGCCCCACCACCCA TGAGT |
| SEQ ID NO: 5 | AS-rs401681-fwdC | CCTTCCTTCCTTCCTTCC TTCCTTGACCTATCCAGA CAACTTCAGAGTCC |
| SEQ ID NO: 6 | AS-rs401681-fwdT | GATCAGGCGTCTGTCGTG CTCGACCTATCCAGACAA CTTCAGAGTCT |
| SEQ ID NO: 7 | AS-rs401681-revA | GATCAGGCGTCTGTCGTG CTCGGTGAAAGCTGCTTC ACACCATGATA |
| SEQ ID NO: 8 | AS-rs401681-revG | CCTTCCTTCCTTCCTTCC TTCCTTTCTAAGCTGCTT CACACCATGATG |
| SEQ ID NO: 9 | AS-rs667282-fwdC | CCTTCCTTCCTTCCTTCC TTCCTTAAACTAACAAGC TCCCAGGTGAC |
| SEQ ID NO: 10 | AS-rs667282-fwdT | GATCAGGCGTCTGTCGTG CTCTAATCTAACAAGCTC CCAGGTGAT |
| SEQ ID NO: 11 | AS-rs667282-revA | GATCAGGCGTCTGTCGTG CTCACAGATACACTGACC AACAGTATTCACA |
| SEQ ID NO: 12 | AS-rs667282-revG | CCTTCCTTCCTTCCTTCC TTCCTTACAGATACACTG ACCAACAGTATTCACG |
| SEQ ID NO: 13 | AS-rs2072590-fwdG | CCTTCCTTCCTTCCTTCC TTCCTTAACAGGGAAGAT GGTACCAGCG |
| SEQ ID NO: 14 | AS-rs2072590-fwdT | GATCAGGCGTCTGTCGTG CTCTAAGAGGGAAGATGG TACCAGCT |
| SEQ ID NO: 15 | AS-rs2072590-revA | GATCAGGCGTCTGTCGTG CTCGACGTGAGCTGAGCT CTAGGGA |
| SEQ ID NO: 16 | AS-rs2072590-revC | CCTTCCTTCCTTCCTTCC TTCCTTACCTGAGCTGAG CTCTAGGGC |
| SEQ ID NO: 17 | AS-rs2131877-fwdC | CCTTCCTTCCTTCCTTCC TTCCTTTTTGCAGGCAGT ATTTACAGAGCAC |
| SEQ ID NO: 18 | AS-rs2131877-fwdT | GATCAGGCGTCTGTCGTG CTCTTTGCAGGCAGTATT TACAGAGCAT |
| SEQ ID NO: 19 | AS-rs2131877-revA | GATCAGGCGTCTGTCGTG CTCACGGCACTCTACATT TAACCTCTCCA |
| SEQ ID NO: 20 | AS-rs2131877-revG | CCTTCCTTCCTTCCTTCC TTCCTTACGGCACTCTAC ATTTAACCTCTCCG |
| SEQ ID NO: 21 | Universal-GC | Cy5-CCTTCCTTCCTTCC TTCCTTCCTT |
| SEQ ID NO: 22 | Universal-AT | Cy3-GATCAGGCGTCTGT CGTGCTC |
| SEQ ID NO: 23 | AS-rs29232 | amine-TTTTTTTTTTAG AGATTATACTTGCAATGC TATCAAAATRCTCATGGG TGGTGGGG |
| SEQ ID NO: 24 | AS-rs401681 | amine-TTTTTTTTTTCT ATCCAGACAACTTCAGAG TCYATCATGGTGTGAAGC AGCTTTC |
| SEQ ID NO: 25 | AS-rs667282 | amine-TTTTTTTTTTTT CTAACAAGCTCCCAGGTG AYGTGAATACTGTTGGTC AGTGTATC |
| SEQ ID NO: 26 | AS-rs2072590 | amine-TTTTTTTTTGA GGGAAGATGGTACCAGCK CCCTAGAGCTCAGCTCAC |
| SEQ ID NO: 27 | AS-rs2131877 | amine-TTTTTTTTTGC AGGCAGTATTTACAGAGC AYGGAGAGGTTAAATGTA GAGTGC |

Regarding the amplified product labeling method for microarray, includes but not limited to a specific modified base, a specific modified primer and a chemical modification, wherein a variety of the specific modified base is added into an amplification reaction, for example: biotin-dCTP, Cy5-dCTP and aminoallyl-dCTP, or the specific modified base is added to the 3' terminus of the amplified product using terminal deoxynucleotidyl transferase, for example: directly adding dCTP modified with fluorescence into the first amplifying section, and the second amplifying section is not require. A variety of the specific modified primer is added into an amplification reaction, for example: fluorescence, biotin, digoxigenin (DIG) and oligonucleotide sequence add to the 5' terminus of the primer. The chemical modification is added after an amplification reaction, fluorescence molecular is directly added to the base of the amplified product by using ULS™ methodology (Kreatech Diagnostics).

EXAMPLE 2

The Effect of SYBR Green onSpecificity

The method of double allele specific polymerase chain reaction (PCR) for single nucleotide polymorphism (SNP) microarray is combined with an interchelating agent during the first amplified section, which can enhance detection specificity.

In one embodiment, SYBR green I (SYBR Green I Nucleic Acid Gel Stain, cat #1988131, ROCHE) is used as the interchelating agent, and respectively diluting to: (1) 25× dilution, (2) 50× dilution, (3) 100× dilution, (4) 200× dilution, (5) 400× dilution, (6) 800× dilution, (7) 1600× dilution, (8) 3200× dilution, (9) 6400× dilution.

In one embodiment, DNA samples, NA12891 and NA18526, are obtained from USA Coriell Institute for Medical Research. For rs29232 genotyping, the database has shown that rs29232 genotyping of NA 12891 is CC, rs29232 genotyping of NA18526 is TT. The primer pair mix of rs29232 includes: AT primer pair mix containing 5 μM each SEQ ID NO:1 and SEQ ID NO:4, and GC primer pair mix containing 5 μM each SEQ ID NO:2 and SEQ ID NO:3.

In addition, the present invention uses different brand SYBR green qPCR master mix: Fast SYBR Green I Master Mix (cat #4385612, APPLIED BIOSYSTEMS), and iQ™ SYBR® Green Superinix (cat #1708880, BIO-RAD).

The real-time polymerase chain reaction condition is as follows: 10 μL total volume comprising: 5 μL SYBR green qPCR master mix, 2 μL SYBR green diluting solution, 1 μL primer pair mix, 1.8 μL water and 0.2 μL gDNA (50 ng/μL). To amplify gDNA using CFX Connect Real-Time PCR Detection System (BIO-RAD LABORATORIES, INC.) for 50 cycles: an initial denaturation 1 min at 95° C., then each cycle including denaturation 10 secs at 95° C., annealing 30 secs at 65° C.

Ct value is obtained from qPCR to calculate ΔCt=(Ct of AT primer pair mix)-(Ct of GC primer pair mix), Table 2 shows the result of ABI Fast SYBR Green I Master Mix. The genotyping of the two samples: NA12891 is CC genotyping, NA18526 is TT genotyping. ΔCt value of CC genotyping obtained from qPCR shows that Ct of GC primer pair mix is less than Ct of AT primer pair mix so as to get a positive value of ΔCt, on the contrary, ΔCt value of TT genotyping obtained from qPCR is a negative value. The larger absolute value shows a higher level of detection specificity. The two absolute values of 100× dilution SYBR green are larger, which indicate that the detection specificity of the two genotyping is good. The absolute values of 50× dilution SYBR green at CC genotyping (NA12891) is lager, but the absolute values of 50× dilution SYBR green at TT genotyping (NA18526) is smaller, which indicate that only CC genotyping shows good detection specificity, and TT genotyping shows poor detection specificity under this diluting condition. Therefore, 100× dilution SYBR green using with ABI Fast SYBR Green I Master Mix has best detection specificity. Table 3 shows the result of BIO-RAD iQ™ SYBR® Green Supermix, wherein 800× to 1600× dilution SYBR green using with BIO-RAD iQ™ SYBR® Green Supermix has best detection specificity. These results indicate that even though different brand qPCR master mix uses with different dilution SYBR green, SYBR green can enhance detection specificity.

EXAMPLE 3

The Effect on Detection Specificity Using Other Interchelating Agent

The inventor uses GelRed™ nucleic acid gel stain (cat #89139-138, BIOTIUM, INC.) as the interchelating agent, and respectively diluting to: (1) 100× dilution, (2) 200× dilution, (3) 400× dilution, (4) 800× dilution, (5) 1600× dilution, (6) 3200× dilution, (7) 6400× dilution, (8) water.

In one embodiment, DNA samples, NA12891 and NA18526, are obtained from USA Coriell Institute for Medical Research. For rs29232 genotyping, the database has shown that rs29232 genotyping of NA 12891 is CC, rs29232 genotyping of NA18526 is TT. The primer pair mix of rs29232 includes: AT primer pair mix containing 5 μM each SEQ ID NO:1 and EQ ID NO:4, and GC primer pair mix containing 5 μM each SEQ ID NO:2 and SEQ ID NO:3.

The real-time polymerase chain reaction condition is as follows: 10 μL total volume comprising: 5 μL Fast SYBR Green I Master Mix, 2 μL GelRed diluting solution, 1 μL primer pair mix, 1.8 μL water and 0.2 μL gDNA (50 ng/μL). To amplify gDNA using CFX Connect Real-Time PCR Detection System (BIO-RAD LABORATORIES, INC.) for 50 cycles: an initial denaturation 1 min at 95° C., then each cycle including denaturation 10 secs at 95° C., annealing 30 secs at 65° C.

Ct value is obtained from qPCR to calculate ΔCt=(Ct of AT primer pair mix)−(Ct of GC primer pair mix), the results are shown in Table 4, as EXAMPLE 2 judgement method, the data of GelRed dilution solution is similar with water. Therefore, GelRed has poor detection specificity, the result indicates that not all interchelating agent can enhance detection specificity.

TABLE 2

ΔCt value of ABI Fast SYBR Green I Master Mix

| | SYBR diluting solution | | | | | | | | |
|---|---|---|---|---|---|---|---|---|---|
| | (1) 25X dilution | (2) 50 X dilution | (3) 100 X dilution | (4) 200 X dilution | (5) 400 X dilution | (6) 800 X dilution | (7) 1600 X dilution | (8) 3200 X dilution | (9) 6400 X dilution |
| NA12891 | NA | 9.28 | 5.73 | 3.05 | 0.91 | 0.87 | 1.59 | 2.83 | 3.57 |
| NA18526 | NA | −1.28 | −5.21 | −3.37 | −2.42 | −2.83 | −4.37 | −5.28 | −5.51 |

TABLE 3

ΔCt value of BIO-RAD iQ ™ SYBR ® Green Supermix

| | SYBR diluting solution | | | | | | | | |
|---|---|---|---|---|---|---|---|---|---|
| | (1) 25X dilution | (2) 50 X dilution | (3) 100 X dilution | (4) 200 X dilution | (5) 400 X dilution | (6) 800 X dilution | (7) 1600 X dilution | (8) 3200 X dilution | (9) 6400 X dilution |
| NA12891 | NA | NA | NA | NA | NA | 6.63 | 6.88 | 4.41 | 4.65 |
| NA18526 | NA | NA | NA | NA | NA | −8.94 | −5.39 | −3.85 | −2.93 |

TABLE 4

ΔCt value of GelRed using with ABI Fast SYBR Green I Master Mix

| | GelRed diluting solution | | | | | | | |
|---|---|---|---|---|---|---|---|---|
| | (1) 100 X dilution | (2) 200 X dilution | (3) 400 X dilution | (4) 800 X dilution | (5) 1600 X dilution | (6) 3200 X dilution | (7) 5400 X dilution | (8) water |
| NA12891 | NA | 2.2 | 2.13 | 1.33 | 1.06 | 1.58 | 1.62 | 1.66 |
| NA18526 | NA | −6.1 | −3.96 | −2.79 | −2.86 | −2.89 | −3.64 | −4.64 |

EXAMPLE 4

The Detection Specificity of Multiplex SNP

The present invention has validated that SYBR green can enhance the detection specificity; the present invention further validates the detection specificity of multiplex SNP by performing multiplex SNP polymerase chain reaction.

In the present embodiment, three SNPs, rs29232, rs401681 and rs667582 are used to detect. rs29232 AT primer pair mix containing 2.5 μM each SEQ ID NO:1 and SEQ ID NO:4 (rs29232), rs401681 AT primer pair mix containing 2.5 μM each SEQ ID NO:6 and SEQ ID NO:7 (rs401681), rs667582 AT primer pair mix containing 2.5 μM each SEQ ID NO:10 and SEQ ID NO:11 (rs667582); rs29232 GC primer pair mix containing 2.5 μM each SEQ ID NO:2 and SEQ ID NO:3 (rs29232), rs401681 GC primer pair mix containing 2.5 μM each SEQ ID NO:5 and SEQ ID NO:8 (r5401681), rs667582 GC primer pair mix containing 2.5 μM each SEQ ID NO:9 and SEQ ID NO:12 (rs667582).

In one embodiment, DNA samples, NA12891, NA18524, NA18526 and NA18558 are obtained from USA Coriell Institute for Medical Research. The database has shown the genotyping of each sample at Table 5.

TABLE 5 the genotyping of each sample

| | NA12891 | NA18524 | NA18526 | NA18558 |
|---|---|---|---|---|
| rs29232 | CC | TC | TT | TC |
| rs401681 | CT | TT | CC | CT |
| rs667282 | CT | TT | TT | CC |

The real-time polymerase chain reaction condition is as follows: 10 μL total volume comprising: 5 μL Bio-Rad iQ™ SYBR® Green Supermix, 0.67 μL SYBR green 320× diluting solution, 2 μL primer pair mix, 2.83 μL water and 0.5 μL gDNA (50 ng/μL). To amplify gDNA using CFX Connect Real-Time PCR Detection System (BIO-RAD LABORATORIES, INC.) for 50 cycles: an initial denaturation 1 min at 95° C., then each cycle including denaturation 10 secs at 95° C., annealing 30 secs at 65° C.

The genotyping of each sample is same as Table 5 shown, which indicates that the method of double allele specific polymerase chain reaction (PCR) for single nucleotide polymorphism (SNP) microarray has high accuracy for multiplex SNP detection. In addition, Ct value is obtained from qPCR to calculate ΔCt=(Ct of AT primer pair mix)−(Ct of GC primer pair mix), as shown in Table 6, SYBR green not only can enhance the detection specificity for single SNP, but also can enhance the detection specificity for multiplex SNP.

TABLE 6

| | ΔCt of each sample | | |
|---|---|---|---|
| | rs29232 | rs401681 | rs667282 |
| NA12891 | 8.80 | 0.13 | −2.83 |
| NA18524 | −1.58 | −12.49 | −11.74 |
| NA18526 | −7.15 | 7.92 | −9.43 |
| NA18558 | −1.97 | −1.61 | 6.44 |

EXAMPLE 5

SNP Microarray Test

The method of double allele specific polymerase chain reaction (PCR) for single nucleotide polymorphism (SNP) microarray, in one embodiment, is to detect rs29232, rs401681, rs667582, rs2072590 and rs2131877, the first amplified section is to amplify SNP variation sites (using SEQ ID NO:1 to SEQ ID NO:20) for obtaining a first amplified product; the second amplified section is to amplify the first amplified product using universal primers (SEQ ID NO:21 and SEQ ID NO:22) for obtaining an second amplified product; and determine the identity of SNP using a SNP microarray fixing probes (SEQ ID NO:23 to SEQ ID NO:27).

Wherein AT primer pair mix contains 1.5 μM each SEQ ID NO:1, SEQ ID NO:4, SEQ ID NO:6, SEQ ID NO:7, SEQ ID NO:10, SEQ ID NO:11, SEQ ID NO:14, SEQ ID NO:15, SEQ ID NO:18 and SEQ ID NO:19; and GC primer pair mix contains 1.5 μM each SEQ ID NO:2, SEQ ID NO:3, SEQ ID NO:5, SEQ ID NO:8, SEQ ID NO:9, SEQ ID NO:12, SEQ ID NO:13, SEQ ID NO:16, SEQ ID NO:17 and SEQ ID NO:20.

In one embodiment, DNA samples, NA12891, NA18524, NA18526 and NA18559 are obtained from USA Coriell Institute for Medical Research. The database has shown the genotyping of each sample at Table 7.

TABLE 7 the genotyping of each sample

| | NA12891 | NA18524 | NA18526 | NA18529 |
|---|---|---|---|---|
| rs2072590 | CC | CA | CA | CC |
| rs2131877 | GG | AA | AA | GA |
| rs29232 | CC | TC | TT | TC |
| rs401681 | CT | TT | CC | CC |
| rs667282 | CT | TT | TT | CT |

The first amplified section is as follows: Two separated reactions (labeled A & B) of 10 μL total volume comprising: 5 μL ABI Fast SYBR Green I Master Mix, 1.5 μL SYBR green 100× diluting solution, 1.5 μL primer pair mix (A reaction using AT primer pair mix, and B reaction using GC primer pair mix) and 2 µL gDNA (50 ng/µL). To amplify gDNA using ABI Thermal Cycler (GeneAmp® PCR System 9700, ABI) for 16 cycles: an initial denaturation 1 min at 95° C., then each cycle including denaturation 10 secs at 95° C., annealing 30 secs at 65° C., and the reaction is stopped at 4° C.

The second amplified section is as follows: 30 µL total volume comprising: 10 µL the first amplified product, 10 µL ABI Fast SYBR Green I Master Mix, 1.0 µL universal primer pair mix (10 µM) and 9 µL water. Wherein the AT universal primer (SEQ ID NO: 21) and GC universal primer (SEQ ID NO: 22) is respectively performed in different reaction, and labeled with A and B. To amplify the first amplified product using ABI Thermal Cycler (GeneAmp® PCR System 9700, ABI) for 30 cycles: an initial denaturation 1 min at 95° C., then each cycle including denaturation 10 secs at 95° C., annealing 30 secs at 70° C., and the reaction is stopped at 4° C. Finally mixing A and B reaction product to perform the step of hybridizing with SNP microarray.

The second amplified product is added into the solution of 100 µL hybridization buffer (containing 4.27 M tetramethylammonium chloride solution, 0.9% EMPIGEN BB detergent, 100 mM Tris buffer (pH 8.0)) and 50 µL formamide, then mixing well. Heating the mixing solution at 80° C. for 5 mins and cooling at 4° C. for 5 mins Loading the cooled solution into a SNP microarray fixing probes (SEQ ID NO: 23 to SEQ ID NO: 27), incubating the SNP microarray at 45° C. and rotating at 2 rpm overnight. Performing washing step, washing with 42° C. wash buffer I (2× SSPE butter, containing 0.1% SDS) using a horizontal shaker at 80 rpm for 3 mins, and washing with 42° C. wash buffer II (0.1× SSPE butter, containing 0.1% SDS) using a horizontal shaker at 80 rpm for 3 mins, then washing with room temperature wash buffer III (0.1× SSPE butter) using a horizontal shaker at 80 rpm for 5 mins; drying the SNP microarray. Finally scanning the SNP microarray, the present invention use CapitalBio's LuxScan™ 10k/A Microarray Scanner having two excitation lasers 635 nm (PMT 750V) and 532 nm (PMT 600V) to scan, and analyzing the image files with Genepix 4.0 image analysis software (Axon Laboratory).

Calculating $\log_2$ ratio by the formula: AT(signal intensity-background intensity)/GC(signal intensity-background intensity), $\log_2$ ratio of homozygote G or C genotype is a negative value, $\log_2$ ratio of homozygote A or T genotype is a positive value, $\log_2$ ratio of heterozygote is between the two homozygote values. As shown in Table 8, the genotyping of each sample is same as well-known genotyping, this result validates that the method of double allele specific polymerase chain reaction (PCR) for single nucleotide polymorphism (SNP) microarray has high accuracy, and indicates the method can identify multiplex SNP in one-tube reaction.

TABLE 8

| $\log_2$ ratio of each sample | | | | |
|---|---|---|---|---|
| | NA12891 | NA18524 | NA18526 | NA18529 |
| rs2072590 | −6.30 | 1.06 | 1.25 | −6.83 |
| rs2131877 | −0.85 | 5.22 | 4.57 | 2.67 |

TABLE 8-continued

| $\log_2$ ratio of each sample | | | | |
|---|---|---|---|---|
| | NA12891 | NA18524 | NA18526 | NA18529 |
| rs29232 | −7.13 | −1.11 | 1.91 | −1.24 |
| rs401681 | 1.98 | 4.83 | −6.30 | −2.96 |
| rs667282 | 2.43 | 4.37 | 4.74 | 1.89 |

In addition, adding modified label at 5' terminus of SNP variation site primer pairs to directly perform the first amplifying section, and it is not require to perform the second amplifying section; or, there is no any modification in the amplified product, it can detect whether any product hybridizing on the surface of a SNP microarray using a method similar with surface plasmon resonance (SPR).

Moreover, when a single SNP site has over two kinds of genotype, as shown in Table 9, a barcode sequence can add at the 5' terminus of the allele specific primer, and a SNP microarray fixing probe containing the sequence complementary to the barcode sequence, and the amplified reaction is performed as EXAMPLE 5, the result of hybridization can show two kinds of SNP signal (as shows in Table 9, A class and B class), A class probe can identify the first barcode sequence, and B class probe can identify the second barcode sequence. Calculating A class $\log_2$ ratio of rad to green fluorescence signals to identify the A or G genotype, or B class $\log_2$ ratio of rad to green fluorescence signals to identify the T or C genotype.

TABLE 9

| identify the barcode sequence at 5' allele specific primer | | | | |
|---|---|---|---|---|
| Genotype | A | T | G | C |
| Reaction tube | NO. 1 | NO. 1 | NO. 2 | NO. 2 |
| dCTP | Cy3-dCTP | Cy3-dCTP | Cy5-dCTP | Cy5-dCTP |
| Barcode sequence | First barcode sequence | Second barcode sequence | First barcode sequence | Second barcode sequence |
| Probe | A class | B class | A class | B class |

In summary, the present invention is to provide a method of double allele specific primer for single nucleotide polymorphism (SNP) microarray, the method is to use the allele specific site as the 3' terminal nucleotide of forward and reverse primers, it does not require a primer having specific nucleotides, and is easily to design the primer based on flanking region of the allele specific site, and to perform multiplex SNP PCR using with an interchelating agent. The method can efficiently reduce the time of the pre-treatment step of hybridization the amplified product with the SNP microarray to 5 hr, and reduce the cost of synthetic specific nucleotide primer compared to commercial SNP array protocol. The method of the present invention also has the advantages of detecting a plurality of SNPs at the same time; therefore, it is an effective, fast, low-cost, large-scale SNP genotyping detection technology.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A method of double allele specific polymerase chain reaction (PCR) for single nucleotide polymorphism (SNP) microarray, comprising:
  (a) amplifying a nucleic acid sample by multiplex SNP PCR using at least a primer set which recognizes a single nucleotide polymorphism (SNP) to obtain an amplified product; wherein an interchelating agent is added into PCR to inhibit non-specific amplification, and the interchelating agent is N',N'-dimethyl-N-[4-[(E)-(3-methyl-1,3-benzothiazol-2-ylidene)methyl]-1-phenylquinolin-1-ium-2-yl]-N-propylpropane-1,3-diamine; and
  (b) contacting the amplified product with a SNP microarray fixed probe suitable for determining the identity of SNP to genotype SNP,
  wherein the primer set contains at least four allele specific primers, which at least two allele specific primers bound with a sense strand of the nucleic acid sample, and 3' terminal nucleotides of the two allele specific primers are complementary to an allele specific site; and at least two allele specific primers bound with an antisense strand of the nucleic acid sample, and 3' terminal nucleotides of the two allele specific primers are complementary to the allele specific site;
  wherein the allele specific primers have melting temperature (Tm) values, and the Tm values have maximum temperature difference of 2.8° C. in single PCR.

2. The method according to claim 1, wherein the nucleic acid sample is obtained from blood, serum, plasma, body fluids or tissues.

3. The method according to claim 1, wherein the SNP microarray is detected by a fluorescent array imaging reader.

4. The method according to claim 1, wherein a 5' terminal end of the allele specific primer further comprises a modified label.

5. The method according to claim 1, further comprising adding a specific modified base during the multiplex SNP PCR amplification.

6. A method of double allele specific polymerase chain reaction (PCR) for single nucleotide polymorphism (SNP) microarray by identifying a modified label, comprising:
  (a) amplifying a nucleic acid sample by multiplex SNP PCR using at least a primer set which recognizes a single nucleotide polymorphism (SNP) to obtain a first amplified product; wherein an interchelating agent is added into PCR to inhibit non-specific amplification, and the interchelating agent is N',N'-dimethyl-N-[4-[(E)-(3-methyl-1,3-benzothiazol-2-ylidene)methyl]-1-phenylquinolin-1-ium-2-yl]-N-propylpropane-1,3-diamine;
  (b) amplifying the first amplified product using a universal PCR primer having a modified label at 5'terminal end to obtain a second amplified product; and
  (c) contacting the second amplified product with a SNP microarray fixed probe suitable for determining the identity of SNP to genotype SNP,
  wherein the sequence of the primer set contains two regions, which 5' terminal region of the allele specific primer is a universal PCR primer sequence, and 3' terminal region of the allele specific primer is an allele specific primer region; and
  wherein the primer set contains at least four allele specific primers, which at least two allele specific primers bound with a sense strand of the nucleic acid sample, and the 3' terminal region of the two allele specific primers are complementary to an allele specific site; and at least two allele specific primers bound with an antisense strand of the nucleic acid sample, and the 3' terminal region of the two allele specific primers are complementary to the allele specific site;
  wherein the allele specific primers have melting temperature (Tm) values, and the Tm values have maximum temperature difference of 2.8° C. in single PCR.

7. The method according to claim 6, wherein the modified label is fluorescence, biotin, digoxigenin (DIG) or oligonucleotide sequence.

8. The method according to claim 6, wherein the nucleic acid sample is obtained from blood, serum, plasma, body fluids or tissues.

9. The method according to claim 6, wherein the allele specific primers further comprise a barcode sequence between the universal PCR primer sequence and the allele specific primer region; and the probe of step (c) comprises a sequence complementary to the barcode sequence.

10. The method according to claim 6, wherein the SNP microarray is detected by a fluorescent array imaging reader.

* * * * *

SEQUENCE LISTING

<160> NUMBER OF SEQ ID NOS: 27

<210> SEQ ID NO 1
<211> LENGTH: 54
<212> TYPE: DNA
<213> ORGANISM: Artificial Sequence
<220> FEATURE:
<223> OTHER INFORMATION: Synthetic primer

<400> SEQUENCE: 1
gatcaggcgt ctgtcgtgct ctggagagat tatacttgca atgctatcaa aata    54

<210> SEQ ID NO 2
<211> LENGTH: 57
<212> TYPE: DNA
<213> ORGANISM: Artificial Sequence
<220> FEATURE:
<223> OTHER INFORMATION: Synthetic primer

<400> SEQUENCE: 2
ccttccttcc ttccttcctt cctttggaga gattatactt gcaatgctat caaaatg    57

<210> SEQ ID NO 3
<211> LENGTH: 43
<212> TYPE: DNA
<213> ORGANISM: Artificial Sequence
<220> FEATURE:
<223> OTHER INFORMATION: Synthetic primer

<400> SEQUENCE: 3
ccttccttcc ttccttcctt ccttaggccc accacccatg agc    43

<210> SEQ ID NO 4
<211> LENGTH: 41
<212> TYPE: DNA
<213> ORGANISM: Artificial Sequence
<220> FEATURE:
<223> OTHER INFORMATION: Synthetic primer

<400> SEQUENCE: 4
gatcaggcgt ctgtcgtgct ctagccccac cacccatgag t    41

<210> SEQ ID NO 5
<211> LENGTH: 50
<212> TYPE: DNA
<213> ORGANISM: Artificial Sequence
<220> FEATURE:
<223> OTHER INFORMATION: Synthetic primer

<400> SEQUENCE: 5
ccttccttcc ttccttcctt ccttgaccta tccagacaac ttcagagtcc    50

<210> SEQ ID NO 6
<211> LENGTH: 47
<212> TYPE: DNA
<213> ORGANISM: Artificial Sequence
<220> FEATURE:
<223> OTHER INFORMATION: Synthetic primer

<400> SEQUENCE: 6
gatcaggcgt ctgtcgtgct cgacctatcc agacaacttc agagtct    47

<210> SEQ ID NO 7
<211> LENGTH: 47
<212> TYPE: DNA
<213> ORGANISM: Artificial Sequence
<220> FEATURE:
<223> OTHER INFORMATION: Synthetic primer

<400> SEQUENCE: 7
gatcaggcgt ctgtcgtgct cggtgaaagc tgcttcacac catgata          47

<210> SEQ ID NO 8
<211> LENGTH: 48
<212> TYPE: DNA
<213> ORGANISM: Artificial Sequence
<220> FEATURE:
<223> OTHER INFORMATION: Synthetic primer

<400> SEQUENCE: 8
ccttccttcc ttccttcctt cctttctaag ctgcttcaca ccatgatg         48

<210> SEQ ID NO 9
<211> LENGTH: 47
<212> TYPE: DNA
<213> ORGANISM: Artificial Sequence
<220> FEATURE:
<223> OTHER INFORMATION: Synthetic primer

<400> SEQUENCE: 9
ccttccttcc ttccttcctt ccttaaacta acaagctccc aggtgac          47

<210> SEQ ID NO 10
<211> LENGTH: 45
<212> TYPE: DNA
<213> ORGANISM: Artificial Sequence
<220> FEATURE:
<223> OTHER INFORMATION: Synthetic primer

<400> SEQUENCE: 10
gatcaggcgt ctgtcgtgct ctaatctaac aagctcccag gtgat            45

<210> SEQ ID NO 11
<211> LENGTH: 49
<212> TYPE: DNA
<213> ORGANISM: Artificial Sequence
<220> FEATURE:
<223> OTHER INFORMATION: Synthetic primer

<400> SEQUENCE: 11
gatcaggcgt ctgtcgtgct cacagataca ctgaccaaca gtattcaca        49

<210> SEQ ID NO 12
<211> LENGTH: 52
<212> TYPE: DNA
<213> ORGANISM: Artificial Sequence
<220> FEATURE:
<223> OTHER INFORMATION: Synthetic primer

<400> SEQUENCE: 12
ccttccttcc ttccttcctt ccttacagat acactgacca acagtattca cg    52

<210> SEQ ID NO 13
<211> LENGTH: 46
<212> TYPE: DNA
<213> ORGANISM: Artificial Sequence
<220> FEATURE:
<223> OTHER INFORMATION: Synthetic primer

<400> SEQUENCE: 13
ccttccttcc ttccttcctt ccttaacagg gaagatggta ccagcg           46

<210> SEQ ID NO 14
<211> LENGTH: 44
<212> TYPE: DNA
<213> ORGANISM: Artificial Sequence
<220> FEATURE:
<223> OTHER INFORMATION: Synthetic primer

<400> SEQUENCE: 14
gatcaggcgt ctgtcgtgct ctaagaggga agatggtacc agct                    44

<210> SEQ ID NO 15
<211> LENGTH: 43
<212> TYPE: DNA
<213> ORGANISM: Artificial Sequence
<220> FEATURE:
<223> OTHER INFORMATION: Synthetic primer

<400> SEQUENCE: 15
gatcaggcgt ctgtcgtgct cgacgtgagc tgagctctag gga                     43

<210> SEQ ID NO 16
<211> LENGTH: 45
<212> TYPE: DNA
<213> ORGANISM: Artificial Sequence
<220> FEATURE:
<223> OTHER INFORMATION: Synthetic primer

<400> SEQUENCE: 16
ccttccttcc ttccttcctt ccttacctga gctgagctct agggc                   45

<210> SEQ ID NO 17
<211> LENGTH: 49
<212> TYPE: DNA
<213> ORGANISM: Artificial Sequence
<220> FEATURE:
<223> OTHER INFORMATION: Synthetic primer

<400> SEQUENCE: 17
ccttccttcc ttccttcctt cctttttgca ggcagtattt acagagcac               49

<210> SEQ ID NO 18
<211> LENGTH: 46
<212> TYPE: DNA
<213> ORGANISM: Artificial Sequence
<220> FEATURE:
<223> OTHER INFORMATION: Synthetic primer

<400> SEQUENCE: 18
gatcaggcgt ctgtcgtgct ctttgcaggc agtatttaca gagcat                  46

<210> SEQ ID NO 19
<211> LENGTH: 47
<212> TYPE: DNA
<213> ORGANISM: Artificial Sequence
<220> FEATURE:
<223> OTHER INFORMATION: Synthetic primer

<400> SEQUENCE: 19
gatcaggcgt ctgtcgtgct cacggcactc tacatttaac ctctcca                 47

<210> SEQ ID NO 20
<211> LENGTH: 50
<212> TYPE: DNA
<213> ORGANISM: Artificial Sequence
<220> FEATURE:
<223> OTHER INFORMATION: Synthetic primer -continued

<400> SEQUENCE: 20
ccttccttcc ttccttcctt ccttacggca ctctacattt aacctctccg                50

<210> SEQ ID NO 21
<211> LENGTH: 24
<212> TYPE: DNA
<213> ORGANISM: Artificial Sequence
<220> FEATURE:
<223> OTHER INFORMATION: Synthetic primer

<400> SEQUENCE: 21
ccttccttcc ttccttcctt cctt                                            24

<210> SEQ ID NO 22
<211> LENGTH: 21
<212> TYPE: DNA
<213> ORGANISM: Artificial Sequence
<220> FEATURE:
<223> OTHER INFORMATION: Synthetic primer

<400> SEQUENCE: 22
gatcaggcgt ctgtcgtgct c                                               21

<210> SEQ ID NO 23
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 23
tttttttttt agagattata cttgcaatgc tatcaaaatr ctcatgggtg gtgggg         56

<210> SEQ ID NO 24
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 24
tttttttttt ctatccagac aacttcagag tcyatcatgg tgtgaagcag ctttc          55

<210> SEQ ID NO 25
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 25
tttttttttt ttctaacaag ctcccaggtg aygtgaatac tgttggtcag tgtatc         56

<210> SEQ ID NO 26
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 26
tttttttttt gagggaagat ggtaccagck ccctagagct cagctcac                  48

<210> SEQ ID NO 27

```
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 27
tttttttttt gcaggcagta tttacagagc ayggagaggt taaatgtaga gtgc          54
```